US005637500A

United States Patent [19]

Sih

[11] Patent Number: 5,637,500
[45] Date of Patent: Jun. 10, 1997

[54] PROCESS FOR PREPARING OPTICALLY ACTIVE ALPHA-HYDROXYALKENE DERIVATIVES

[75] Inventor: Charles J. Sih, Madison, Wis.

[73] Assignee: Suntory Limited, Osaka, Japan

[21] Appl. No.: 311,885

[22] Filed: Sep. 26, 1994

Related U.S. Application Data

[63] Continuation of Ser. No. 944,738, Sep. 14, 1992, abandoned, which is a continuation of Ser. No. 567,065, Aug. 13, 1990, abandoned.

[51] Int. Cl.[6] ................................ C12P 7/62; C12P 7/04; C12P 41/00
[52] U.S. Cl. ........................... 435/280; 435/135; 435/157
[58] Field of Search .................................. 435/280, 134, 435/135, 157

[56] References Cited

U.S. PATENT DOCUMENTS

| | | | |
|---|---|---|---|
| 4,745,066 | 5/1988 | Hamaguchi et al. | 435/280 |
| 4,963,492 | 10/1990 | Keller et al. | 435/280 |
| 5,128,264 | 7/1992 | Sih | 435/280 |

FOREIGN PATENT DOCUMENTS

| | | | |
|---|---|---|---|
| 0118428 | 9/1980 | Japan . | |
| 3214198 | 9/1988 | Japan | 435/157 |
| 2-39898 | 2/1990 | Japan . | |
| 2-39899 | 2/1990 | Japan . | |

OTHER PUBLICATIONS

Langrand, G. et al., Tetrahed. Letts 27: 29–32 (1986).
Baratti G. et al, Proc. World Conf. Emerging Technol. Fats Oils Ind., Eds Baldwin A et al, Am Oil Chem. Soc pp. 355–358 (1986).
Cambou B et al, Biotech of Bioengin. XXVI: 1449–54 (1984).
Journal of the American Chemical Society, vol. 104, 1982, Washington, DC CH.–S. Chen et al "Quantitative Analyses of Biochemical Kinetic Resolutions of Enantiomers" pp. 7294–7299.

*Primary Examiner*—David M. Naff
*Assistant Examiner*—S. Saucier
*Attorney, Agent, or Firm*—Oblon, Spivak, McClelland, Maier & Neustadt, P.C.

[57] ABSTRACT

A process for preparing optically active 1-substituted-3-hydroxy-1-butene or its derivatives of formula (II) or (III)

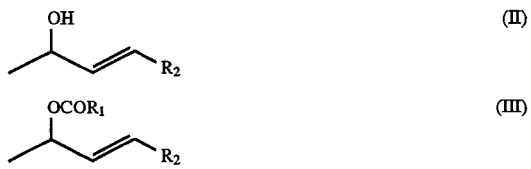

is disclosed. The process comprises treating an ester derivative of racemic 1-substituted-3-hydroxy-1-butene of formula (I),

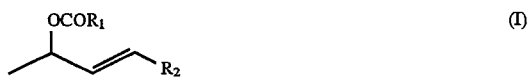

wherein $R_1$ is a substituted or unsubstituted alkyl, aryl, alkoxy, or aryloxy group, and $R_2$ is a hydrogen atom, halogen atom, an alkyl, aryl, alkoxy or aryloxy group, or a substituted or unsubstituted alkylsulfonyloxy, arylsulfonyloxy, alkylthio, or arylthio group. The process can produce a desired optically active alcohol or acyl-protected compound at a high yield and a high selectivity under mild conditions by the treatment of the substrate with a lipase. In particular, when $R_1$=methyl and $R_2$=halogen or phenylthio, use of Lipase AK, P-30 or K-10 gives high enantiomeric purity.

4 Claims, No Drawings

PROCESS FOR PREPARING OPTICALLY ACTIVE ALPHA-HYDROXYALKENE DERIVATIVES

This application is a Continuation of application Ser. No. 07/944,738, filed on Sep. 14, 1992, now abandoned, which is a continuation of Ser. No. 07/567,065, filed Aug. 13, 1990, now abandoned.

BACKGROUND OF THE INVENTION

1. Field of the Invention

The present invention relates to a process for preparing optically active 1-substituted-3-hydroxy-1-butene or its ester derivatives, and, more particularly, to a process for preparing optically active 1-substituted-3-hydroxy-1-butene or its ester derivatives which comprises treating racemic 1-substituted-3-hydroxy-1-butene or its ester derivatives with a lipase.

The products of the present invention can be used, for example, as a raw material of azetidinone compounds disclosed in Japanese Patent Application Laid-open No. 207373/1986. The inexpensive and simple preparation of the compounds is expected to make great contributions to the development in this field.

2. Description of the Background Art

The demand for optically active compounds are increasing in recent years in such areas as pharmaceuticals, agrichemicals, cosmetics, liquid crystals, and the like. Because synthesis of optically active compounds have been handicapped in terms of the production cost and the technology, the research in this area have remained only at a preliminary stage. The recent increase in their demands, however, has advanced the technology for their synthesis, offering more opportunities for their use.

A conventional process for producing optically active compounds involves selective reduction of carbonyl compounds. High prices of reducing agents and the requirements of special procedures in their handling have been problems in such a conventional process. A process in which microorganisms or enzymes produced therefrom are used, on the other hand, have had still to be improved in the selectivity, the reaction substrate concentration, and the like in order to apply them to a commercial production.

According to the process of the present invention in which an alcohol compound protected by an acyl group is used as a substrate can produce a desired optically active alcohol or its acyl-protected derivative in a high yield and in high optical purity under mild conditions by the treatment of the acylated alcohol substrate with a lipase. The process can provide a high substrate concentration at a small consumption of a lipase, and can be adaptable to large scale industrial production.

In view of this situation, the present inventors have undertaken extensive studies, and have found that an optically active 1-substituted-3-hydroxy-1-butene or its derivative represented by formula (II) or (III),

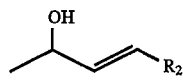 (II)

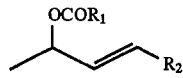 (III)

could be prepared in a high yield and a high selectivity by a simple process in which an ester derivative of racemic 1-substituted-3-hydroxy-1-butene of formula (I),

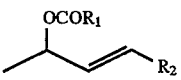 (I)

is treated with a lipase to effect asymmetric hydrolysis.

In the above formulae (I) to (III), $R_1$ is an alkyl group having 1–8 carbon atoms, an aryl group having 6–10 carbon atoms, an alkoxy group having 1–6 carbon atoms, or an aryloxy group having 6–10 carbon atoms, wherein hydrogen atoms on the carbon atoms of the alkyl, aryl, alkoxy, or aryloxy group may optionally be substituted by alkyl, aryl, hydroxyl, alkoxy, alkylthio, or arylthio group, and $R_2$ is a hydrogen atom, an alkyl group having 1–8 carbon atoms, an aryl group having 6–10 carbon atoms, a halogen atom, an alkoxy group having 1–6 carbon atoms, an aryloxy group having 6–10 carbon atoms, an alkylsulfonyloxy group having 1–8 carbon atoms, an arylsulfonyloxy group having 6–10 carbon atoms, an alkylthio group having 1–8 carbon atoms, or an arylthio group having 6–10 carbon atoms, wherein hydrogen atoms on the carbon atoms of the alkylsulfonyloxy, arylsulfonyloxy, alkylthio, or the arylthio group may optionally be substituted by halogen, alkyl, aryl, hydroxyl, or alkoxy group, and in formulae (II) and (III) the secondary hydroxyl group has either R or S configuration.

SUMMARY OF THE INVENTION

Accordingly, an object of the present invention is to provide a process for preparing an optically active 1-substituted-3-hydroxy-1-butene or its derivative represented by formula (II) or (III),

 (II)

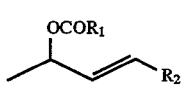 (III)

wherein $R_1$ is an alkyl group having 1–8 carbon atoms, an aryl group having 6–10 carbon atoms, an alkoxy group having 1–6 carbon atoms, or an aryloxy group having 6–10 carbon atoms, wherein hydrogen atoms on the carbon atoms of the alkyl, aryl, alkoxy, or aryloxy group may optionally be substituted by alkyl, aryl, hydroxyl, alkoxy, alkylthio, or arylthio group, and $R_2$ is a hydrogen atom, an alkyl group having 1–8 carbon atoms, an aryl group having 6–10 carbon atoms, a halogen atom, an alkoxy group having 1–6 carbon atoms, an aryloxy group having 6–10 carbon atoms, an alkylsulfonyloxy group having 1–8 carbon atoms, an arylsulfonyloxy group having 6–10 carbon atoms, an alkylthio group having 1–8 carbon atoms, or an arylthio group having 6–10 carbon atoms, wherein hydrogen atoms on the carbon atoms of the alkylsulfonyloxy, arylsulfonyloxy, alkylthio, or the arylthio group may optionally be substituted by halogen, alkyl, aryl, hydroxyl, or alkoxy group, and the secondary hydroxyl group has either R or S configuration, which comprises treating an ester derivative of racemic 1-substituted-3-hydroxy-1-butene of formula (I),

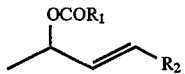 (I)

wherein $R_1$ and $R_2$ have the same meanings as defined above, with a lipase.

Other objects, features, and advantages of this invention will appear more fully from the following description.

DETAILED DESCRIPTION OF THE INVENTION AND PREFERRED EMBODIMENTS

There are a number of reports about the assymetric hydrolysis of racemic compounds using lipase. Few of them, however, have confirmed their efficiency quantitatively, nor few processes have been developed to a commercially competent stage. The present inventors have conducted studies about quantitative analysis of enzymatic or biological resolution products, and contributed a report dealing with the relationship between the extent of conversion (c), the optical purity or enantiometric excess (ee) of the product), and the enantiometric ratio (E value) [J. Amer. Chem. Soc. 104, 7294 (1982)]. The effect of the present invention have specifically been proven by the calculation of the E value according to the following equation.

$$E = \ln[1-c(1+ee(P))]/\ln[1-c(1-ee(P))]$$

wherein,

E (E value): enantiometric ratio c (%): extent of conversion ee(P): enantiometric excess (ee) of the product An ester derivative of racemic secondary alcohol represented by formula (I) can be prepared by a conventional esterification process. A typical example is a condensation reaction of an alcohol represented by formula (IV),

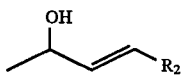 (IV)

wherein $R_2$ has the same meaning as defined above, and a carboxylic acid of the formula $R_1COOH$, wherein $R_1$ has the same meaning as defined above, in the presence of an organic acid such as p-toluenesulfonic acid or the like or a mineral acid such as hydrochloric acid, sulfuric acid, or the like. Alternatively, instead of a carboxylic acid, a carboxylic acid halide, a carboxylic ester, or carboxylic acid anhydride of formula (VI),

 (VI)

wherein $R_1$ has the same meaning as defined above and Y is a halogen atom, an alkoxy group, or an acyloxy group, can be used for the condensation reaction with the alcohol of formula (IV) in the presence of an organic base such as triethylamine or the like or an inorganic base such as sodium hydroxide.

There are no specific restrictions as to the carboxylic acids, acid halides, esters, or acid anhydrides represented by formula (V) or (VI). Preferable compounds are linear alkyl carboxylic acids, e.g. acetic acid, propionic acid; branched alkyl carboxylic acids, e.g. isobutyric acid, pivalic acid; aryl carboxylic acid, e.g. benzoic acid; aralkyl phenyl; aralkyl carboxylic acid, e.g. phenylacetic acid; and acid halides, esters, or acid anhydrides derived from these carboxylic acids. The type of carboxylic acid is determined by the type of lipase used.

The reaction of a compound of formula (I) with a lipase is usually carried out in a buffer solution at temperature, preferably, of 20°–50° C. Although there are no specific restrictions as to the pH of the buffer solution, an optimum pH is selected depending on the type of lipase used. Lipases derived from microorganisms are preferable, with particularly preferable lipases being those derived from the genus Pseudomonas. There are no specific restrictions as to the purity of the lipase used. For example, cultured living cells or deceased cells, either purified or unpurified, can be used.

The amount of lipase used is selected from the range of 0.0001 to 100% by weight, and the concentration of the reaction substrate is selected from the range of 10 to 200%. The reaction time is about 5 to 100 hours, although it is variable depending on the type of lipase and the type of substrate used.

After completion of the reaction, the reaction mixture is extracted with a solvent which is not soluble in water, and the extract is dried and concentrated to give a mixture of the target optically active alcohol and an ester derivative which is the enantiomer of the alcohol. The alcohol and the ester are separated from each other and purified by means of silica gel column chromatography, distillation, or the like.

Alternatively, the reaction mixture is left to stand to separate the oil layer and the water layer, following which the oil layer is washed several times with water or a water soluble solvent to obtain an almost pure ester as the residual oil.

An alcohol, e.g. methanol, ethanol; a ketone, e.g. acetone, methyl vinyl ketone; an ether, e.g. tetrahydrofuran; a nitrile, e.g. acetonitrile; or the like can be used as a water soluble solvent.

The mother liquor obtained in the above procedure can be collected and concentrated to give oil components contained therein. When the ester is contained in the oil components, an additional amount of the ester compound is produced by repeting the above procedure. In this way, the target alcohol compound can be obtained ultimately in an almost pure form. Since this fractional extraction method can produce the target alcohol compound or ester without procedures such as chromatography, distillation, or the like, it can be applied more advantageously to large scale production of unstable compounds or compounds for which a high degree of purification is not required.

Other features of the invention will become apparent in the course of the following description of the exemplary embodiments which are given for illustration of the invention and are not intended to be limiting thereof.

EXAMPLES

Example 1

Into a suspension of 120 mg of (±)-3-acetoxy-1-(phenylthio)-1-butene in 2 ml of 0.2M phosphate buffer (pH 8), 30 mg of lipase shown in Table 1 below was added, and the mixture was stirred at 24° C. until a conversion rate of about 50% was achieved, upon which ethyl acetate was added to separate the water layer and the organic layer. The organic layer was dried over anhydrous sodium sulfate, and concentrated under a reduced pressure. The residue was purified over silica gel column chromatography to produce a pure ester compound and alcohol compound. The enantiometric excess purity (ee %) of the ester compound was determined by the measurement of 200 M Hz PMR in the presence of $Eu(hfc)_3$. The results are given in Table 1.

TABLE 1

| Lipase | Reaction time (hr) | Ester compound Absolute configuration | ee % | Alcohol compound Absolute configuration | ee % | c Value (%) | E Value |
|---|---|---|---|---|---|---|---|
| K-10 | 15.5 | S | 26 | R | 91 | 22 | 27 |
| AK | 15.5 | S | 35 | R | 86 | 29 | 19 |
| P-30 | 15 | S | 86 | R | 96 | 47 | >100 |

Obviously, numerous modifications and variations of the present invention are possible in light of the above teachings. It is therefore to be understood that within the scope of the appended claims, the invention may be practiced otherwise than as specifically described herein.

What is claimed is:

1. A process for preparing an optically active 1-substituted 3-hydroxy-1-butene compound represented by formula (II) having an R configuration

(II)

wherein $R_2$ is a halogen atom or a phenylthio group comprising treating an ester of racemic 1-substituted-3-hydroxy-1-butene of formula (I),

(I)

wherein $R_1$ is a methyl group and $R_2$ has the same meanings as defined above, with a lipase obtained from the genus Pseudomonas and selected from the group consisting of Lipase K-10, AK and P-30; and recovering the optically active product from the resolving medium.

2. The process according to claim 1, wherein the ester of formula (I) is treated in a buffer solution.

3. The process according to claim 1, wherein the ester of formula (I) is treated in a buffer solution at a temperature of about 20° to about 50° C.

4. The process according to claim 3, wherein the ester of formula (I) is treated in a buffer solution at a temperature of about 24° C. for about 15 to about 15.5 hours.

* * * * *